(12) United States Patent
Helmer

(10) Patent No.: US 11,565,051 B2
(45) Date of Patent: Jan. 31, 2023

(54) SENSOR SYSTEM

(71) Applicant: SANOFI, Paris (FR)

(72) Inventor: Michael Helmer, Frankfurt am Main (DE)

(73) Assignee: Sanofi, Paris (FR)

(*) Notice: Subject to any disclaimer, the term of this patent is extended or adjusted under 35 U.S.C. 154(b) by 286 days.

(21) Appl. No.: 16/768,143

(22) PCT Filed: Nov. 28, 2018

(86) PCT No.: PCT/EP2018/082847
§ 371 (c)(1),
(2) Date: May 29, 2020

(87) PCT Pub. No.: WO2019/106014
PCT Pub. Date: Jun. 6, 2019

(65) Prior Publication Data
US 2020/0384201 A1 Dec. 10, 2020

(30) Foreign Application Priority Data
Dec. 1, 2017 (EP) .................................. 17306678

(51) Int. Cl.
A61M 5/315 (2006.01)
(52) U.S. Cl.
CPC .... *A61M 5/31511* (2013.01); *A61M 5/31566* (2013.01); *A61M 2205/3317* (2013.01); *A61M 2205/3327* (2013.01); *A61M 2205/3569* (2013.01); *A61M 2205/502* (2013.01)

(58) Field of Classification Search
CPC .............. A61M 5/315; A61M 5/31566; A61M 2205/3317; A61M 2205/3327; A61M 2205/3569
See application file for complete search history.

(56) References Cited

U.S. PATENT DOCUMENTS

| 4,471,304 A | 9/1984 | Wolf |
| 2007/0062251 A1 | 3/2007 | Anex |
| 2008/0058732 A1* | 3/2008 | Harris ................. A61M 5/2425 604/235 |

(Continued)

FOREIGN PATENT DOCUMENTS

| CN | 101868179 | 10/2010 |
| CN | 103108665 | 5/2013 |

(Continued)

OTHER PUBLICATIONS

PCT International Preliminary Report on Patentability in International Appln. No. PCT/EP2018/082847, dated Jun. 2, 2020, 7 pages.

(Continued)

*Primary Examiner* — Bradley J Osinski
(74) *Attorney, Agent, or Firm* — Fish & Richardson P.C.

(57) ABSTRACT

The disclosure relates to a sensor system for detecting a position of a movable plunger in a drug delivery device, the sensor system comprising a sensor capable of detecting a magnetic field, the sensor adapted to be fixed within a housing of a drug delivery device, and a ferromagnetic or permanent magnetic component magnetically interacting with the sensor and adapted to move relative to the sensor as the plunger is moved.

20 Claims, 6 Drawing Sheets

(56) References Cited

U.S. PATENT DOCUMENTS

2012/0022458 A1    1/2012   Oh et al.
2016/0213834 A1*   7/2016   Brady ............... A61M 5/31568
2017/0286638 A1*  10/2017   Searle .............. A61M 5/16831
2020/0326209 A1*  10/2020   Houfburg ................ G01D 5/20

FOREIGN PATENT DOCUMENTS

| CN | 104519931 | 4/2015 |
| CN | 104968380 | 10/2015 |
| CN | 106068164 | 11/2016 |
| CN | 106714878 | 5/2017 |
| WO | WO 2004/038440 | 5/2004 |
| WO | WO 2011/133724 | 10/2011 |
| WO | WO 2014/023763 | 2/2014 |
| WO | WO 2014/118107 | 8/2014 |
| WO | WO 2015/139775 | 9/2015 |
| WO | WO 2016/050902 | 4/2016 |
| WO | WO 2017/029032 | 2/2017 |

OTHER PUBLICATIONS

PCT International Search Report and Written Opinion in International Appln. No. PCT/EP2018/082847, dated Jan. 22, 2019, 10 pages.

* cited by examiner

SENSOR SYSTEM

CROSS REFERENCE TO RELATED APPLICATIONS

The present application is the national stage entry of International Patent Application No. PCT/EP2018/082847, filed on Nov. 28, 2018, and claims priority to Application No. EP 17306678.8, filed on Dec. 1, 2017, the disclosures of which are incorporated herein by reference.

TECHNICAL FIELD

The disclosure generally relates to a sensor system for detecting a position of a movable plunger in a drug delivery device.

BACKGROUND

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional injection devices may deliver the entire contents of a syringe/cartridge or may provide a predetermined or set dose. Conventional injection devices can lack mechanisms to ensure accurate dose delivery. For example, when the entire contents of the syringe/cartridge are intended to be delivered, a residual amount may remain which either means that a full dose was not delivered or the syringe/cartridge must be overfilled to ensure a proper dose is administered. As a further example, when the predetermined/set dose is delivered, over- or under-dosing may occur.

For purposes of user compliance it may be desirable to detect a position of a plunger in a drug delivery device.

Thus, there remains a need for an improved sensor system for detecting a position of a movable plunger in a drug delivery device.

SUMMARY

An object of the present disclosure is to provide

The object is achieved by a sensor system according to claim 1.

Exemplary embodiments are provided in the dependent claims.

According to the present disclosure, a sensor system for determining a position of a movable plunger in a drug delivery device comprises:

a sensor capable of detecting a magnetic field, the sensor adapted to be fixed within a housing of a drug delivery device, and a ferromagnetic or permanent magnetic component magnetically interacting with the sensor and adapted to move relative to the sensor as the plunger is moved.

This allows detecting a position of the plunger within the drug delivery device.

In an exemplary embodiment, the sensor may be embedded in a spring mandrel adapted to be inserted into a drive spring to stabilize the drive spring. The drive spring may in turn be arranged within the plunger.

In an exemplary embodiment, the sensor may comprise at least one electromagnetic coil and/or at least one surface mounted device and/or at least one printed circuit and/or at least one conductive polymer and/or at least one double coil sensor and/or at least one permanent magnetic linear contactless displacement sensor.

In an exemplary embodiment, the sensor is electrically connected to at least two contacts accessible by a control unit to process data acquired by the sensor.

In an exemplary embodiment, the at least two contacts are located at a proximal end of the spring mandrel.

In an exemplary embodiment, the ferromagnetic or permanent magnetic component is a magnetic area in or on the plunger.

In an exemplary embodiment, the magnetic area is a permanent magnet embedded in the plunger or comprises permanent magnetic particles within a polymer material of the plunger.

In an exemplary embodiment, the ferromagnetic or permanent magnetic component is a drive spring comprising a magnetically permeable material.

In an exemplary embodiment, the sensor system may be part of a drug delivery device, further comprising a housing adapted to receive a medicament cartridge, a plunger adapted to advance a piston within the medicament cartridge.

In an exemplary embodiment, the spring mandrel is a separate part or part of the housing or of a proximal end cap connectable to the housing.

In an exemplary embodiment, the control unit is arranged in or on the housing.

According to an aspect of the present disclosure, an add-on device for a drug delivery device may be adapted to be coupled to the housing of the drug delivery device and to be electrically connected to the contacts, the add-on device comprising the control unit.

In an exemplary embodiment, the add-on device comprises a sleeve part configured to be arranged over the proximal end of the housing.

In an exemplary embodiment, the control unit comprises a user interface.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
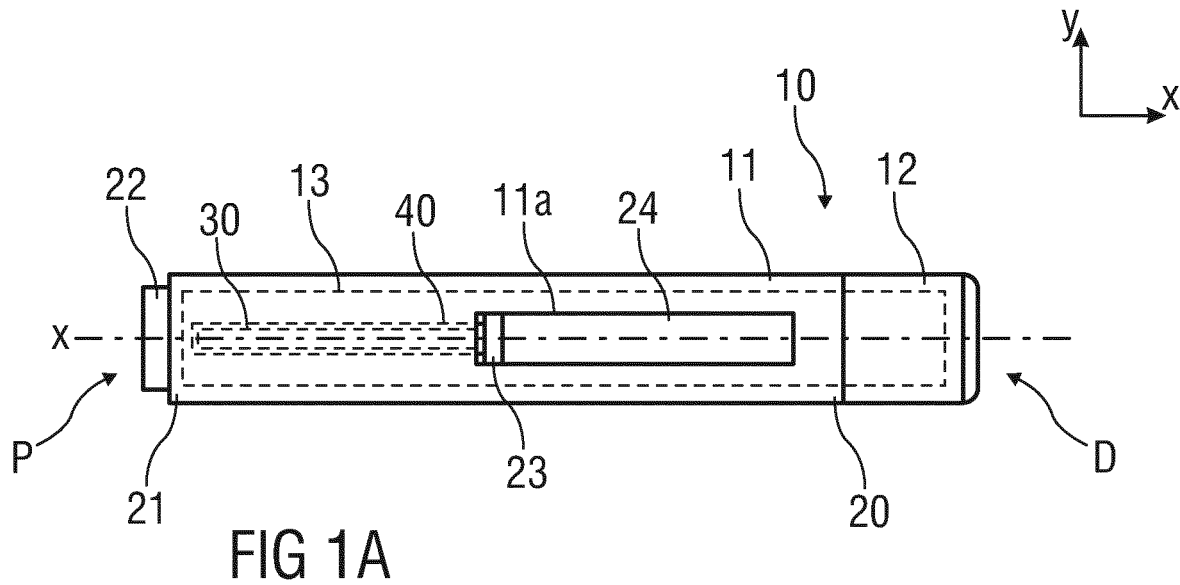
FIG. 1 is a schematic view of a drug delivery device.
Figure 1B:
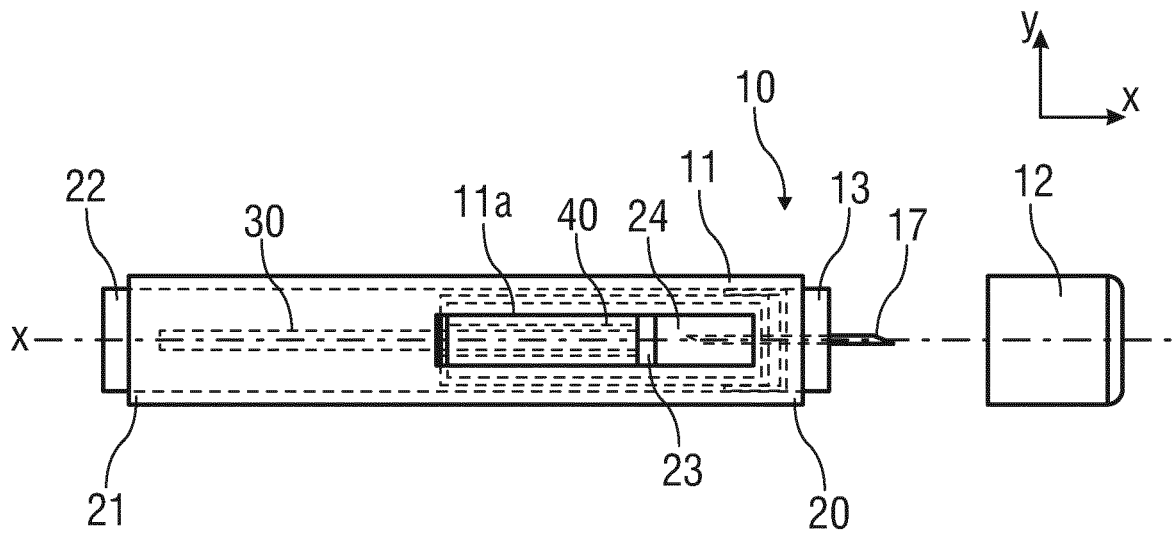

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11.

Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

The drug delivery device 10 may be divided in two subassemblies, a control subassembly and a drive subassembly 10.1. This allows for improving flexibility as to the time and location of manufacture of the subassemblies and final assembly with the syringe 24.

Figure 2:
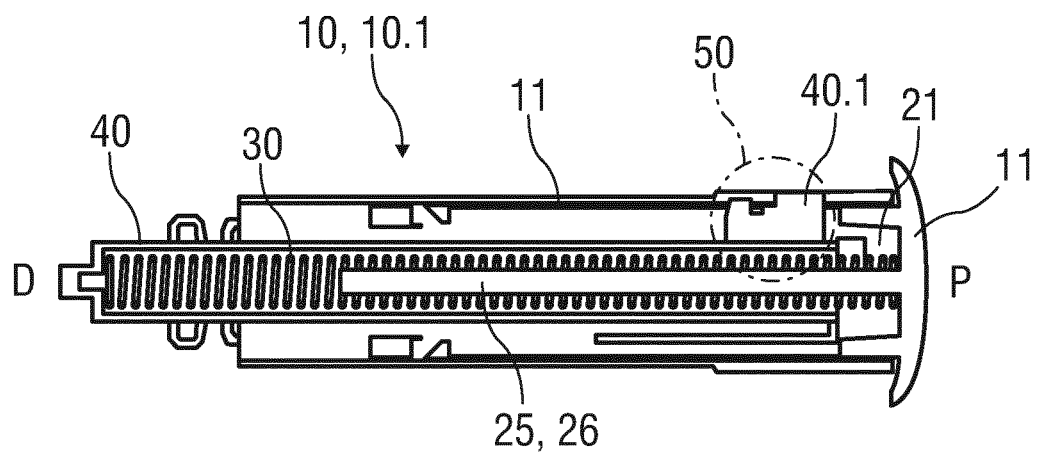
FIG. 2 is a schematic view of a part of a drug delivery device.

FIG. 2 is a schematic view of a part of a drug delivery device 10, e.g. a drive subassembly 10.1. A drive spring 30 is arranged in a plunger 40 and is under compression before the device 10 is activated. A proximal end of the drive spring 30 can be fixed within a proximal region 21 of the housing 11, and a distal end of the drive spring 30 can be configured to apply a compressive force to a proximal surface of piston 23.

A plunger release mechanism 50 may be provided for controlling activation of syringe emptying. The plunger release mechanism 50 may be adapted to release the plunger 40 once the sleeve 13 is depressed and reaches a retracted position within the housing 11.

The plunger release mechanism 50 may comprise a first plunger boss 40.1 arranged on the plunger 40 and a profiled slot (not shown) in the proximal region 21 of the housing 11. The profiled slot may comprise an angled surface adapted to engage the first plunger boss to induce a torque about the longitudinal axis to the plunger 40 to disengage the plunger boss 40.1 from the profiled slot. This rotation may be prevented by a rib on the sleeve 13 as long as it is not in its retracted position. The type of plunger release mechanism 50 is not essential for the present disclosure. Other types of plunger release mechanisms 50 may be applied as well.

A spring mandrel 25 extends from the proximal end of the housing 11 in the distal direction D into the drive spring 30 to stabilize the drive spring 30. The spring mandrel 25 may be a separate part connected to the housing 11. In other embodiments, the spring mandrel 25 may be part of the housing 11. In yet another embodiment, the spring mandrel 25 may be part of a proximal end cap connectable to the housing 11.

In an exemplary embodiment, the spring mandrel 25 comprises a sensor 26 for detecting a magnetic field in order to detect a position of the plunger 40.

Figure 3:
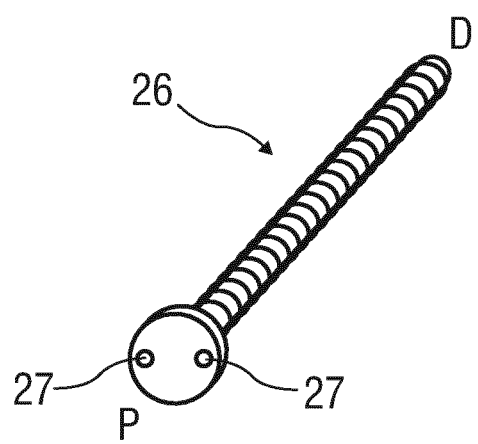
FIG. 3 is a schematic view of a spring mandrel with a sensor.

FIG. 3 is a schematic view of the spring mandrel 25 with the sensor 26.

The sensor 26 may comprise an electromagnetic coil comprising wound wire. In another exemplary embodiment, the sensor 26 may comprise one or more surface mounted devices, e.g. SMD ferrites. In yet another exemplary embodiment, the sensor 26 may comprise a printed circuit. In yet another exemplary embodiment, the sensor 26 may comprise a conductive polymer or printed foil. The sensor 26 may have two or more contacts 27, e.g. at a proximal end of the sensor 26 or spring mandrel 25 which are accessible from outside when the sensor 26 is mounted within the housing 11. This allows for an add-on device to be electrically connected to the sensor 26 to process data acquired by the sensor 26.

Figure 4:
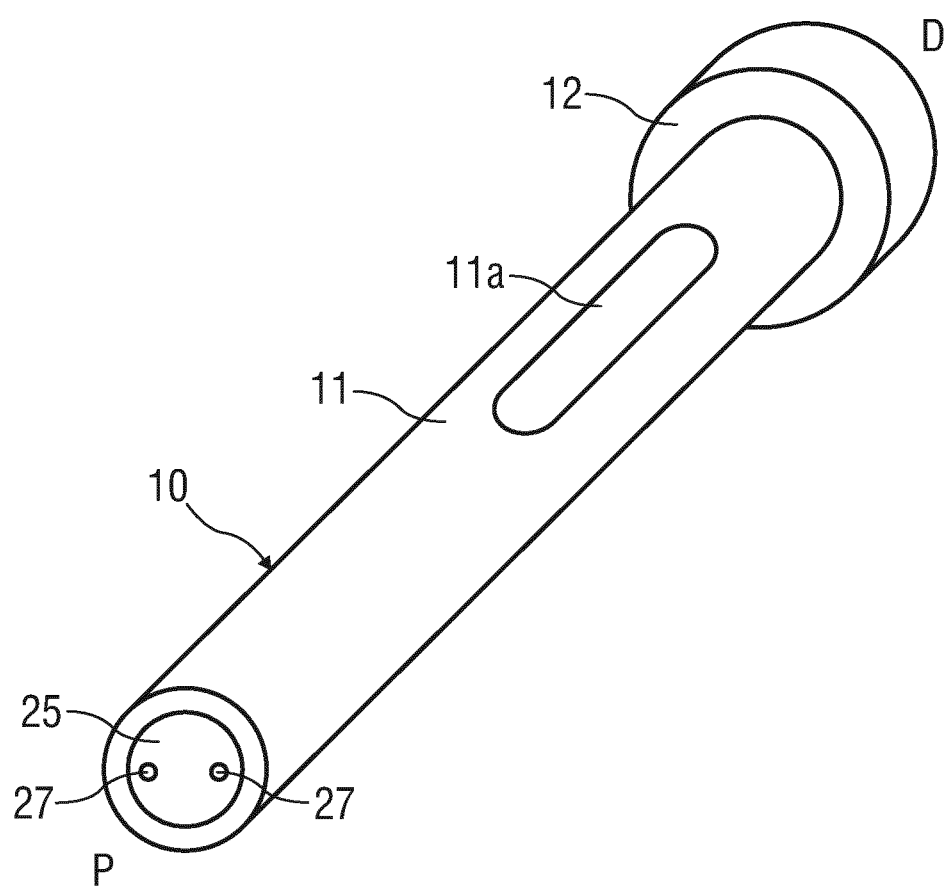
FIG. 4 is a schematic view of a drug delivery device with the spring mandrel inserted.
Figure 5:
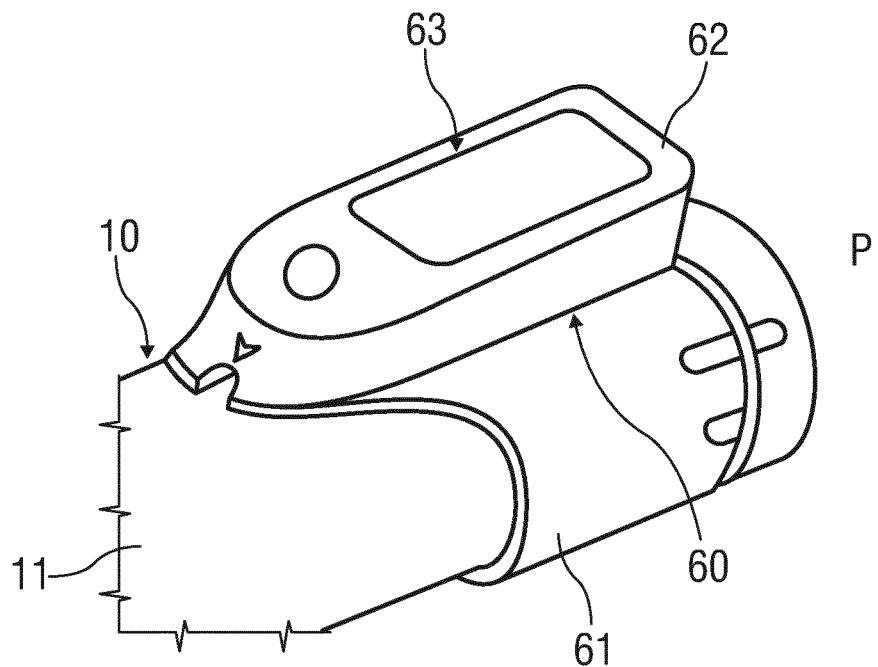
FIG. 5 is a schematic view of an add-on device.

FIG. 4 is a schematic view of a drug delivery device 10 with the spring mandrel 25 comprising the sensor 26 inserted. FIG. 5 is a schematic view of an add-on device 60. The add-on device 60 may comprise a sleeve part 61 configured to be arranged over the proximal end of the housing 11. The add-on device 60 further comprises a control unit 62 comprising a user interface 63 for visually and/or acoustically outputting data to a user and/or for allowing a user to input data. The control unit 62 is configured to be connected to the sensor 26 via the contacts 27 and to process data acquired from the sensor 26.

Figure 6:
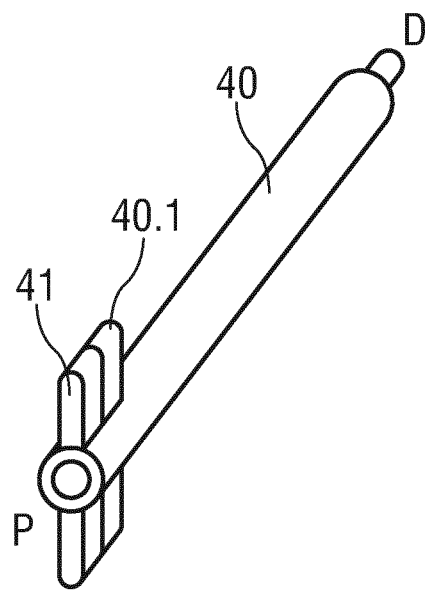
FIG. 6 is a schematic view of a plunger.

FIG. 6 is a schematic view of the plunger 40. In an exemplary embodiment, the plunger 40 may comprise a magnetic area 41, e.g. at a proximal end of the plunger 40. The magnetic area may be a permanent magnet embedded in the material of the plunger 40. In other embodiments, the plunger 40 may comprise permanent magnetic particles within the polymer material of the plunger. The magnetic area 41 on the plunger 40 and the sensor 26 allow for determining an axial position of the plunger 40 within the housing 11.

Figure 7:
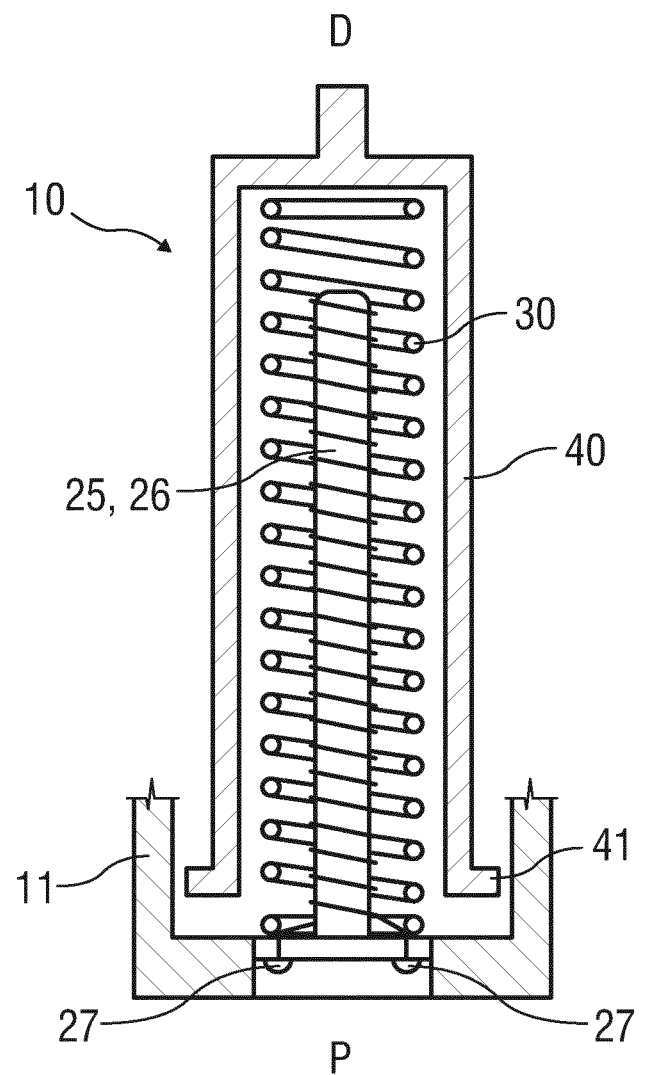
FIG. 7 is a schematic detail view of the drug delivery device prior to an injection.
Figure 8:
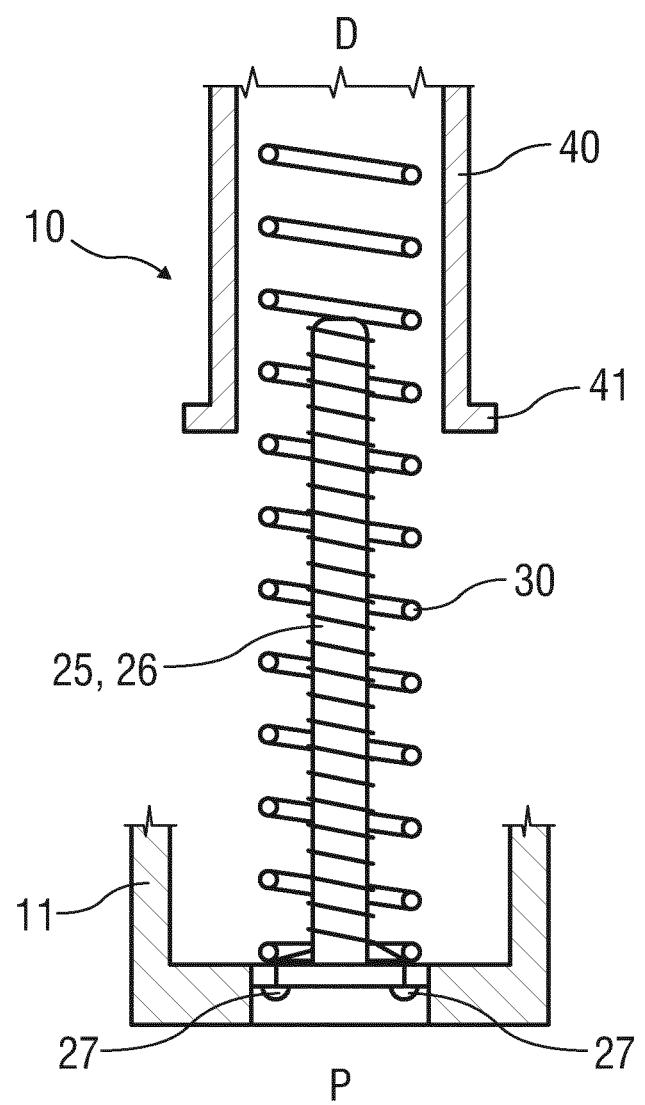
FIG. 8 is a schematic view of the drug delivery device after an injection.

FIG. 7 is a schematic detail view of the drug delivery device 10 prior to an injection. The drive spring 30 is compressed; the plunger 40 is in a retracted position. The magnetic area 41 is located near the proximal end of the drug delivery device 10. The spring mandrel 25 with the sensor 26 is inserted in the housing 11. The sensor 26 is configured as a coil connected to contacts 27. FIG. 8 is a schematic view of the drug delivery device 10 after an injection. The drive spring 30 has been released and the plunger 40 is thus advanced in the distal direction D.

The magnetic area 41 has thus moved along the length of the sensor 26 and induced a current in the coil which may be detected by the add-on device (not shown).

In yet another embodiment, the plunger 40 may not comprise a magnetic area. Instead, the drive spring 30 may comprise or consist of a magnetically permeable material, e.g. a metal, in particular a ferromagnetic metal such as steel, e.g. stainless steel. When the plunger 40 is moved, the drive spring 30 expands so a distance between the windings of the drive spring 30 increases. Due to the magnetic permeability of the drive spring 30, this expansion of the spring will be detected by the sensor 26 as a change in the magnetic field, e.g. as a current induced in the sensor 26 or a resulting voltage. The advantage of this embodiment is the low power consumption of the sensor which may be advantageous for the add-on device.

In another exemplary embodiment, the sensor 26 may be arranged separate from the spring mandrel 25, e.g. outside the drive spring 30. For example, the sensor 26 may be arranged in the plunger 40 or in the housing 11. In these embodiments, a spring mandrel 25 may not be required. The drive spring 30 may be arranged within the plunger 40 or outside the plunger 40.

The sensor 26 or the spring mandrel 25 with the sensor 26 may be configured as a reusable component attachable to a drug delivery device 10, which may be configured as a disposable, one-shot or multi-shot device or as a reusable device.

The sensor 26 may be used by the add-on device 60 to record an injection history, to monitor a dose administration and to assist the patient in setting the injection correctly and in time.

The drug delivery device 10 may be configured to receive either a spring mandrel 25 comprising a sensor 26 or a spring mandrel 25 without a sensor. The plastic spring mandrel can be realized through a changeable tool insert.

In an exemplary embodiment, the control unit 62 may not be arranged in an add-on device but in or on the housing 11.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term 'derivative' refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithochoyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody" as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a poypeptide derived from an antibody polypeptide molecule (e.g., an antibody heavy and/or light chain polypeptide) that does not comprise a full-length antibody poypeptide, but that still comprises at least a portion of a full-length antibody polypeptide that is capable of binding to an antigen. Antibody fragments can comprise a cleaved portion of a full length antibody poypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain poypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and antiIL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES

10 drug delivery device
10.1 drive subassembly
11 housing
11a window
12 cap assembly
13 sleeve
17 needle
20 distal region
21 proximal region
22 button
23 piston
24 syringe
25 spring mandrel
26 sensor
27 contact
30 drive spring
40 plunger 40.1 plunger boss
41 magnetic area
50 plunger release mechanism
60 add-on device
61 sleeve part
62 control unit
63 user interface
D distal end, distal direction
P proximal end, proximal direction
X longitudinal axis

The invention claimed is:

1. A sensor system for detecting a position of a movable plunger in a drug delivery device, the sensor system comprising:
a sensor capable of detecting a magnetic field, the sensor adapted to be fixed within a housing of the drug delivery device; and
a magnetic component magnetically interacting with the sensor and adapted to move relative to the sensor as the movable plunger is moved relative to the sensor, wherein the sensor is embedded in a spring mandrel adapted to be inserted into a drive spring to stabilize the drive spring.

2. The sensor system according to claim 1, wherein the sensor comprises one or more of an electromagnetic coil, a surface mounted device, a printed circuit, a conductive polymer, a double coil sensor, and a permanent magnetic linear contactless displacement sensor.

3. The sensor system according to claim 1, wherein the sensor is electrically connected to at least two contacts accessible by a control unit to process data acquired by the sensor.

4. The sensor system according to claim 3, wherein the at least two contacts are located at a proximal end of the spring mandrel.

5. The sensor system according to claim 1, wherein the magnetic component is a magnetic area in or on the movable plunger.

6. The sensor system according to claim 5, wherein the magnetic area is a permanent magnet embedded in the movable plunger or comprises permanent magnetic particles within a polymer material of the movable plunger.

7. The sensor system according to claim 1, wherein the magnetic component is the drive spring, the drive spring comprising a magnetically permeable material.

8. The sensor system according to claim 1, wherein the magnetic component comprises a ferromagnetic component.

9. The sensor system according to claim 1, wherein the magnetic component comprises a permanent magnetic component.

10. A drug delivery device, comprising:
a housing adapted to receive a medicament cartridge;
a plunger adapted to advance a piston within the medicament cartridge; and
a sensor system for detecting a position of the plunger, the sensor system comprising:
a sensor capable of detecting a magnetic field, the sensor adapted to be fixed within the housing, and
a magnetic component magnetically interacting with the sensor and adapted to move relative to the sensor as the plunger is moved relative to the sensor, wherein the sensor is embedded in a spring mandrel adapted to be inserted into a drive spring to stabilize the drive spring.

11. The drug delivery device according to claim 10, wherein the spring mandrel is part of the housing or of a proximal end cap connectable to the housing.

12. The drug delivery device according to claim 10, wherein a control unit is arranged in or on the housing.

13. The drug delivery device according to claim 10, wherein the magnetic component comprises a ferromagnetic component.

14. The drug delivery device according to claim 10, wherein the magnetic component comprises a permanent magnetic component.

15. The drug delivery device according to claim 10, further comprising the medicament cartridge.

16. An add-on device for a drug delivery device, the drug delivery device comprising:
a housing adapted to receive a medicament cartridge;
a plunger adapted to advance a piston within the medicament cartridge; and
a sensor system for detecting a position of the plunger, the sensor system comprising:
a sensor capable of detecting a magnetic field, the sensor adapted to be fixed within the housing, and
a magnetic component magnetically interacting with the sensor and adapted to move relative to the sensor as the plunger is moved relative to the sensor, wherein the sensor is embedded in a spring mandrel adapted to be inserted into a drive spring to stabilize the drive spring,
wherein the add-on device is adapted to be coupled to the housing and to be electrically connected to at least two contacts of the drug delivery device, and
wherein the add-on device comprises a control unit.

17. The add-on device according to claim 16, further comprising a sleeve part configured to be arranged over the proximal end of the housing.

18. The add-on device according to claim 16, wherein the control unit comprises a user interface.

19. The add-on device according to claim 16, wherein the control unit is configured to process data acquired by the sensor.

20. The add-on device according to claim 16, wherein the control unit is arranged in or on the housing.

* * * * *